US006487434B1

United States Patent

(12) United States Patent
Kaiser et al.
(10) Patent No.: US 6,487,434 B1
(45) Date of Patent: Nov. 26, 2002

(54) MAGNETIC RESONANCE TOMOGRAPH

(75) Inventors: Werner A. Kaiser, St. Augustin (DE); Manfred Selig, Eggenstein-Leopoldshafen (DE); Rudolf Ullrich, Eggenstein-Leopoldshafen (DE); Jörg Vagner, Eggenstein-Leopoldshafen (DE); Siegfried Schönherr, Eggenstein-Leopoldshafen (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 188 days.

(21) Appl. No.: 09/697,574

(22) Filed: Oct. 26, 2000

Related U.S. Application Data

(63) Continuation-in-part of application No. PCT/EP99/02713, filed on Apr. 22, 1999.

(30) Foreign Application Priority Data

Apr. 27, 1998 (DE) ........................................ 198 18 785

(51) Int. Cl.[7] ................................................ A61B 5/05
(52) U.S. Cl. ........................ 600/411; 600/567; 600/568
(58) Field of Search ................................ 600/411, 567, 600/568, 422; 606/130; 324/318

(56) References Cited

U.S. PATENT DOCUMENTS 5,409,497 A 4/1995 Siczek et al.
5,443,068 A 8/1995 Cline et al.
5,534,778 A * 7/1996 Loos et al. ................. 324/318
5,569,266 A * 10/1996 Siczek ........................ 606/130
5,628,327 A 5/1997 Unger et al.
5,678,549 A * 10/1997 Heywang-Koebrunner et al. ............ 600/417
6,094,590 A * 7/2000 Kan et al. ................... 600/411

FOREIGN PATENT DOCUMENTS

EP 0 749 018 12/1996
WO WO 96/08199 3/1996

* cited by examiner

*Primary Examiner*—Teresa Walberg
*Assistant Examiner*—Quang Van
(74) *Attorney, Agent, or Firm*—Klaus J. Bach

(57) ABSTRACT

In a magnetic resonance tomograph having a continuous channel for inserting from one end a stretcher with a female patient lying thereon in a prone position during magnetic resonance mammography, the tomograph is provided with a manipulator by which instruments for the diagnosis and surgical treatment of such patients breasts can be introduced into the channel from the other end and positioned in relation to the breasts which are disposed in the isocenter of the magnetic resonance tomograph. The manipulator has a support arm with a recess for receiving the various instruments which can be installed and exchanged from the other, that is, the proximal end. The support arm with the recess can be pivoted horizontally and vertically about a fixed point located outside the recess and beyond the tip at the distal end of the manipulator adjacent to a breast of the patient.

5 Claims, 7 Drawing Sheets

1
11
23
12
7
6
26, 29
31
47
45
46
52
44
50
53
48
32
49
33
35
51
54
Z
MRT-BETT

MAGNETIC RESONANCE TOMOGRAPH

This is a continuation-in-part application of international application PCT/EP99/02713 filed Apr. 22, 1999 and claiming the priority of German application 198 18 785.8 filed Apr. 27, 1998.

BACKGROUND OF THE INVENTION

The invention relates to a magnetic resonance tomograph without access to the measurement area during a measurement, comprising a continuous channel for inserting from one side a stretcher for use by female patients during magnetic resonance mammography.

In the conventional closed magnetic resonance tomographs (MRT), the MRT mammography with the resulting additional treatment steps such as biopsy and, if necessary, subsequent therapy is performed in a multitude of steps during which the patient needs to be moved several times into, and out of, the channel of the apparatus. Any surgery on the patient can be performed with such a closed magnetic resonance tomograph only outside the apparatus. The procedure is therefore time consuming and results in high physical and psychological stresses of the patient and involves the risk that the position of the patient's breasts changes during the long period of the procedure. The long time required for the procedure also results in high costs for the therapy.

EP-A-0 534 607 discloses a magnetic resonance tomograph with two annular magnets within which the patient rests and between which a mechanical device for the heat treatment of tumors of the patient by laser energy is arranged at one side of the patient. A preceding biopsy is not provided with the MRT according to this publication. It would have to be performed outside the apparatus in some other way. There is no suggestion offered in EPA-0534607 how this situation could be improved.

U.S. Pat. No. 5 443 068 discloses a system for a non-invasive treatment of tumors by local magnetic resonance tomography-supported ultrasonic heating. The system includes a magnetic resonance tomograph (MRT) with a continuous channel into which a stretcher can be introduced from one end thereof. The stretcher includes a manipulator with an ultrasound transducer arranged directly below the support surface of the stretcher. The manipulator has a tub-like support arm, that is, a semi-circular support arm supporting the ultrasonic transducer such that it is movable in all three spatial directions. At the same time, the ultrasonic transducer remains so oriented that it always radiates upwardly. The tub-like support arm also includes a coupling medium, which is necessary for the transmission of the ultrasound waves. For the transmission of the ultrasound waves to a patients body a membrane is disposed on the coupling medium on which membrane the patient is disposed and which conforms to the body of the patient. Lateral movement of the ultrasound transducer in the coupling medium is achieved for each of the spatial axes separately by individual cardanic drive shafts by electric motors, which are arranged outside the MR magnetic field so that they have no influence on the field.

It is the object of the present invention to improve a magnetic resonance tomograph of the type as initially described in such a way that the various diagnosis and treatment steps of the MR mammography can be performed in the apparatus while the patients position remains essentially unchanged and to perform such procedures within a short period of time. The positions of the patient relative to the support and the MR apparatus should remain the same as set up before the start of the procedure for the whole duration of the procedure.

SUMMARY OF THE INVENTION

In a magnetic resonance tomograph comprising a continuous channel for inserting from one end a stretcher with a female patient lying thereon in a prone position during magnetic resonance mammography, the tomograph comprises a manipulator by which instruments for the diagnosis and surgical treatment of such patients breasts can be introduced into the channel from the other end and positioned in relation to the breasts which are disposed in the isocenter of the magnetic resonance tomograph. The manipulator comprises a support arm, which has a recess for receiving the various instruments which can be installed and exchanged from the other, that is, the proximal end. The support arm with the recess can be pivoted horizontally and vertically about a fixed point located outside the recess and beyond the tip at the distal end of the manipulator adjacent to a breast of the patient.

The invention will be described in detail below on the basis of the accompanying drawings.

DESCRIPTION OF THE PREFERRED EMBODIMENT

Figure 3:
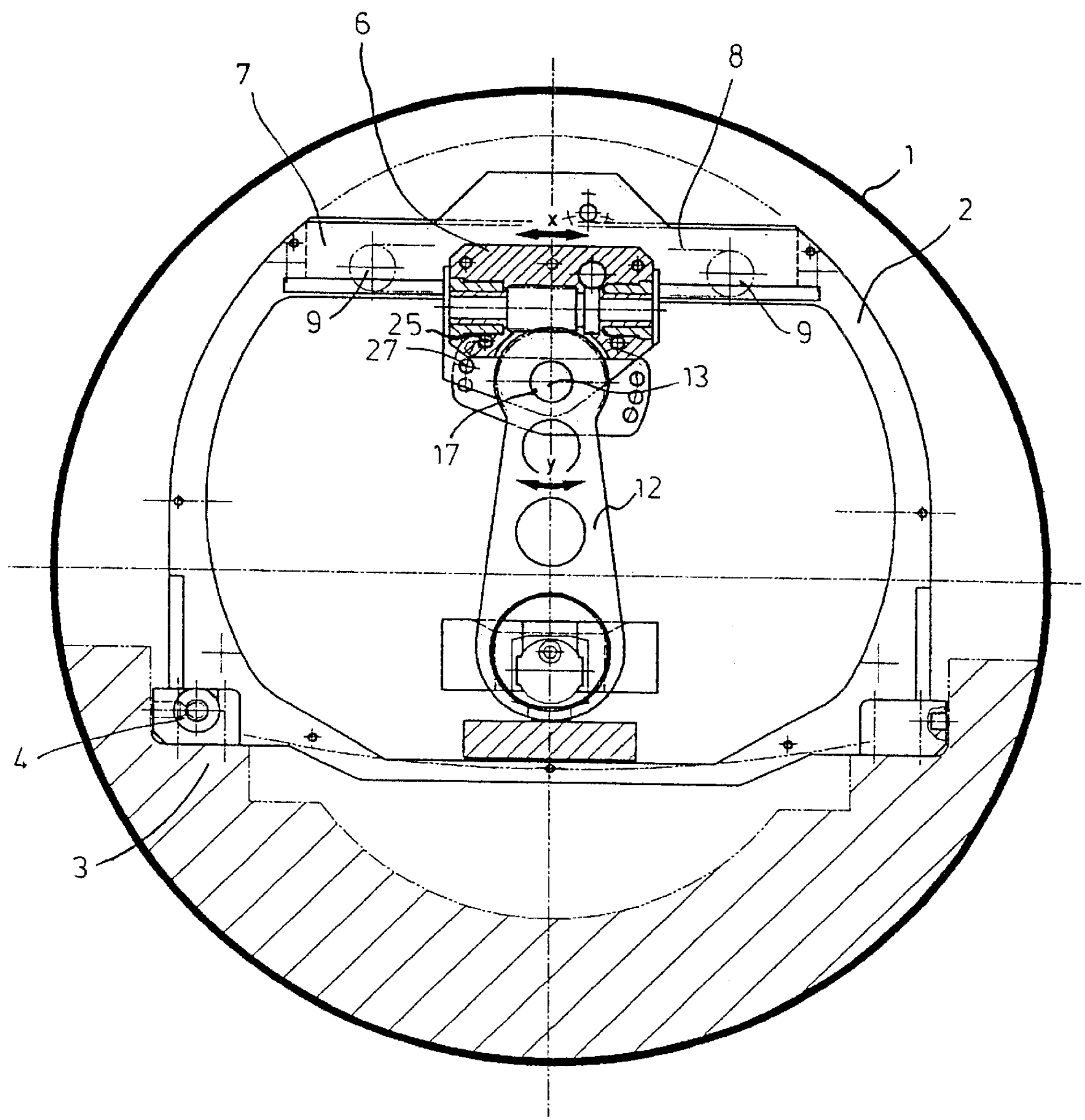
FIG. 3 is a cross-sectional view of the MRT taken along the line A—A with the manipulator disposed in a center position, that is, in its basic position.
Figure 4:
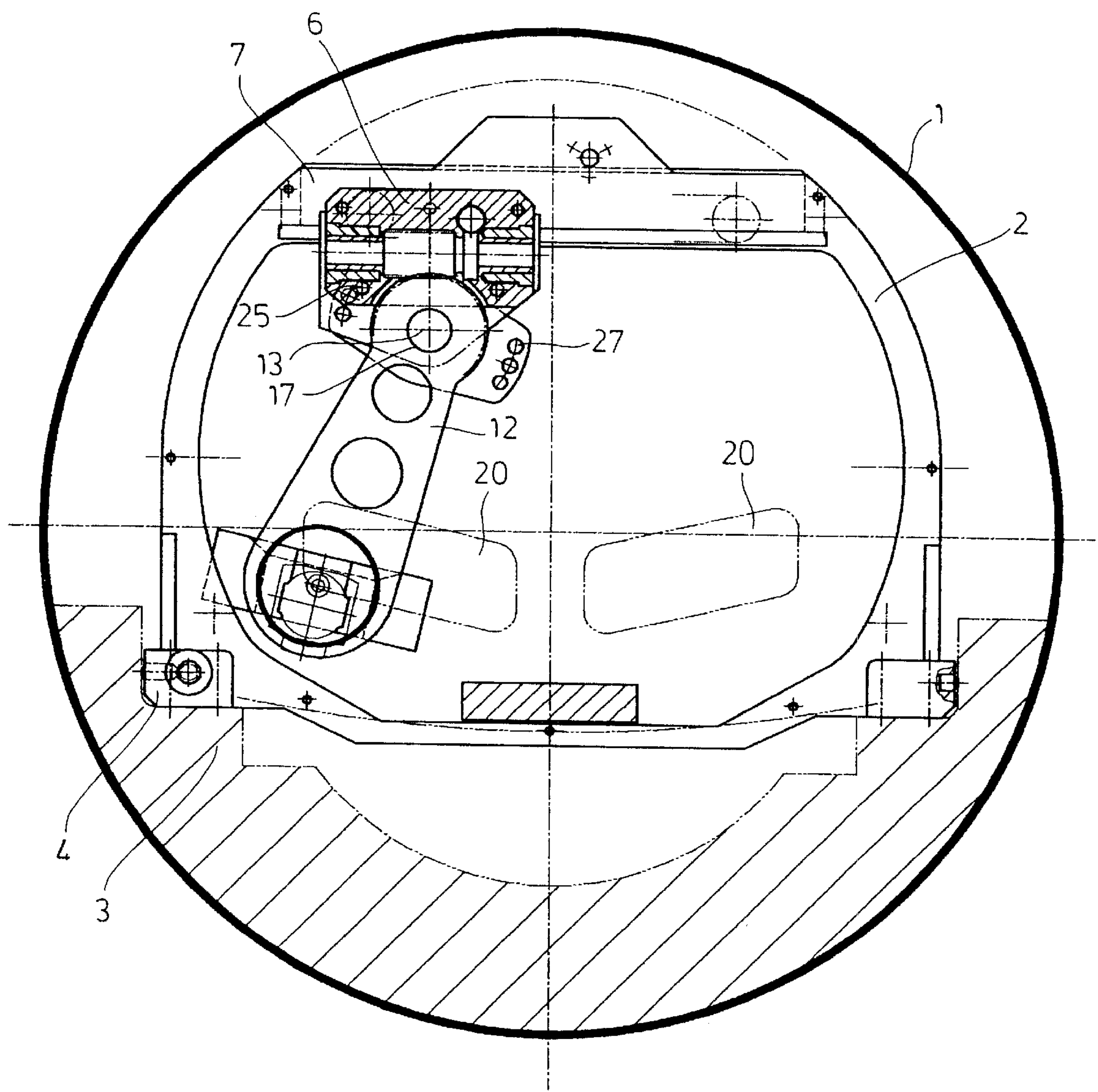
FIG. 4 is a cross-sectional view similar to that of FIG. 3 with the manipulator moved and pivoted to one side.

The manipulator shown in the figures is provided for use in a closed magnetic resonance tomograph (MRT) which includes a continuous channel 1, which is shown in FIGS. 3 and 4, and into which a stretcher (not shown) for supporting a female patient can be introduced for MR mammography and possibly further treatment. The patient is disposed on her stomach.

The different locations of various patient's breasts—resulting from anatomic differences—are all within the area of the windows 20 which are indicated in FIG. 4 and which define the operating area for the manipulator in a vertical plane (x/y range). The breast to be treated is fixed in longitudinal direction in that area by two compression plates so as to be positioned in the iso-center of the MRT. The manipulator is introduced into the MRT from the other end that is from the end of the channel opposite the stretcher until its front end 21 is disposed in the area of the iso-center. In, or at, the front end 21, those instruments are supported which are needed for treatment of the patient. However they are not shown in the figures.

The manipulator must of course consist of materials suitable for use with a MRT. It basically comprises a bow-shaped frame 2, which has at its sides support skids 5 on which it can be moved on tracks 3 into the channel 1 in a longitudinal direction. In the predetermined position, the manipulator can be fixed in the channel 1 by means of a clamping device 4. The pivot arms 12, which will be described later, are in the center position as shown in FIG. 3. In the upper part of the frame 2, there is a conventional bridge 7 on which a horizontally movable carriage 6 is supported and guided by a guide structure so that it is movable in the x-direction. The drive for moving the carriage 6 in the x-direction includes a cable 8 wound onto a cable drum mounted on the carriage 6 and extending around opposite guide pulleys 9 disposed at opposite ends of the bridge 7. The cable drum is driven by a drive shaft 11 by way of a transmission 10.

At the bottom part of the carriage 6, a shaft 17 is rotatably supported and two pivot arms 12 are mounted on the opposite ends of the shaft 17 so as to be rotatable therewith. The pivot arms 12 are pivotable with the shaft 17 about the axis 13 thereof, the pivot movement being indicated as a movement in the direction y. The pivot movement is performed at a respective position of the carriage 6, which is determined by its position in the x-direction. In a particular embodiment of the y-drive as shown in the figures, the upper end of the proximal pivot arm 12 seen in FIG. 3 is provided at its top end above the shaft 17 with a gear segment 18, which is engaged by the worm gear 19 of a transmission 22 that is disposed at the side of the carriage 6 above the pivot arm 12. In this way, the two pivot arms can be pivoted in the y-direction about the axis 13. The transmission 22 includes a drive stub 23 to which a computer-controlled motor is connected, which is not shown. A computer-controlled motor is also connected to the drive shaft 11 for moving the carriage 6 in the x-direction. The movement of the pivot arm 12 in the y-direction occurs by way of the transmission 22.

With the superimposed movements in the x and the y directions, any desired position of the manipulator or, respectively, its tip 21 within the area of the windows 20 can be obtained.

At the end of the shaft 17 opposite the pivot arm with the gear segment 18, there is disposed adjacent the pivot arm 12, a cable pulley 16 which is fixed with respect to the carriage 6 and in which the shaft 17 is rotatable. The cable pulley 16 therefore remains in its position with respect to the carriage 6 when the pivot arms 12 are pivoted. At the ends of the pivot arms 12, remote from the shaft 17, a support tube 14 is rotatably supported by the pivot arms 12. At one end of the support tube 14 outside the pivot arm 12 the support tube carries anther cable pulley 15 in radial alignment with the cable pulley 16 such that the support tube 14 can be rotated by way of a cable 24 extending around the cable pulleys 15 and 16. Preferably, the ends of the cable 24 are clamped to the cable pulleys so that the cable is wound onto one while it is unwound from the other of the pulleys 15 and 16 during pivot movement of the arms 12. Since the cable pulley 16 is fixed in its angular position relative to the carriage 6 by the pin 25, the support tube 14 maintains its angular orientation in the space during pivoting of the arm 12 in the y-direction, that is, it is guided in a horizontal parallel fashion. An orientation of the support tube for an adaptation to a right or left slant of the patient support, which is not shown, is achieved by removal of the pin 25 from a pulley bore 27 and inserting it into another bore 27.

Within the support tube 14, there is a support arm 26, which is an essential element of the manipulator. The support arm 26 is rigidly disposed in, and extends through, the support tube 14 and is movable together therewith. The distal ends form the front end 21 of the manipulator. The end portion projecting from the support tube 14 is hollow so as to form an inner space 28 which extends from the front end 21 backwardly and widens arrow-like. The widening hollow inner space 28 forms the front part of a channel 30, which extends through the support tube 14 up to the proximal end 31 of the support arm 26. At the proximal end 31, the channel 30 consists only of the two side members 29. The channel 30 of the support arm 26 consequently extends from the proximal end 31 all the way to the distal front end 21 of the manipulator. It receives all the instruments necessary for the treatment of a patient which instruments are inserted at the proximal end 31 and extend through the channel 30 to the distal front end 21.

Figure 1:
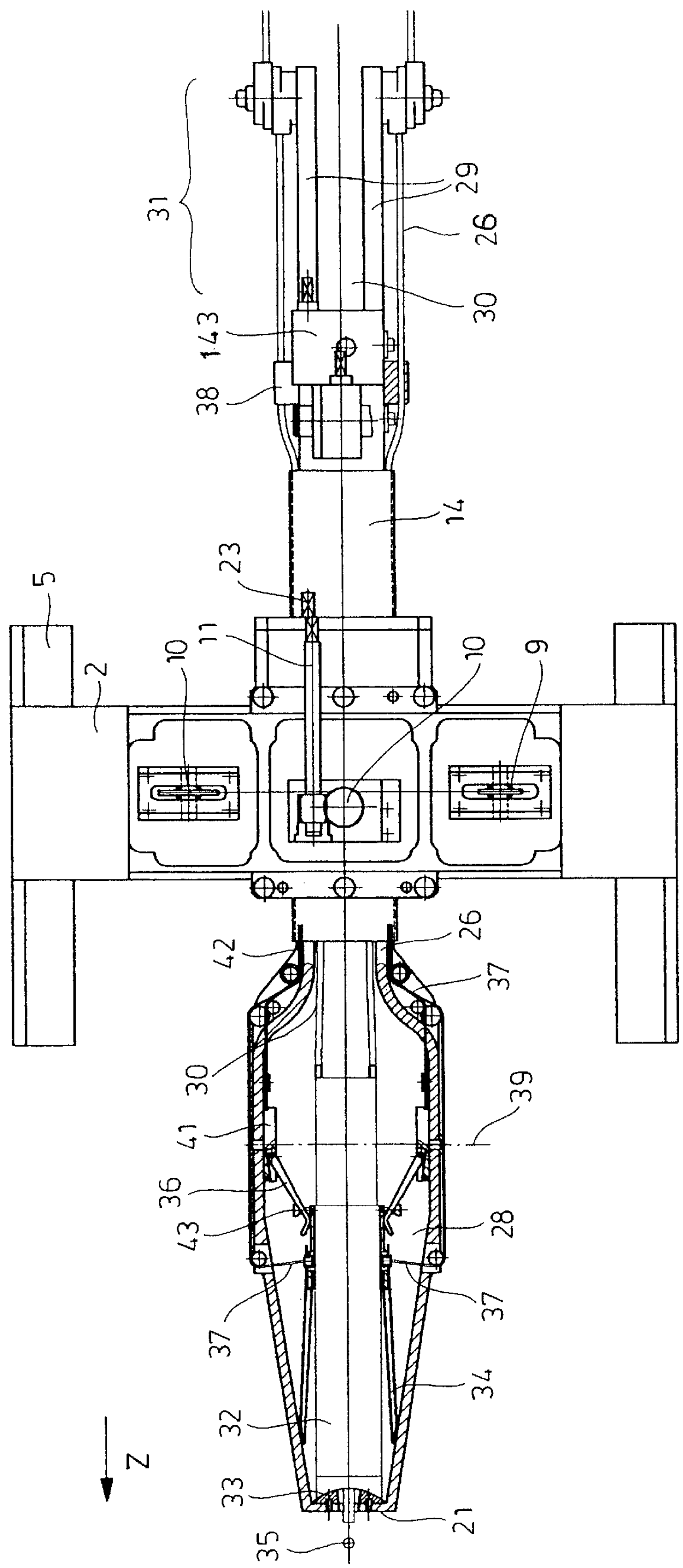
FIG. 1 is a side view of a manipulator for use in a closed magnetic resonance tomograph (MRT) with a continuous channel.
Figure 2:
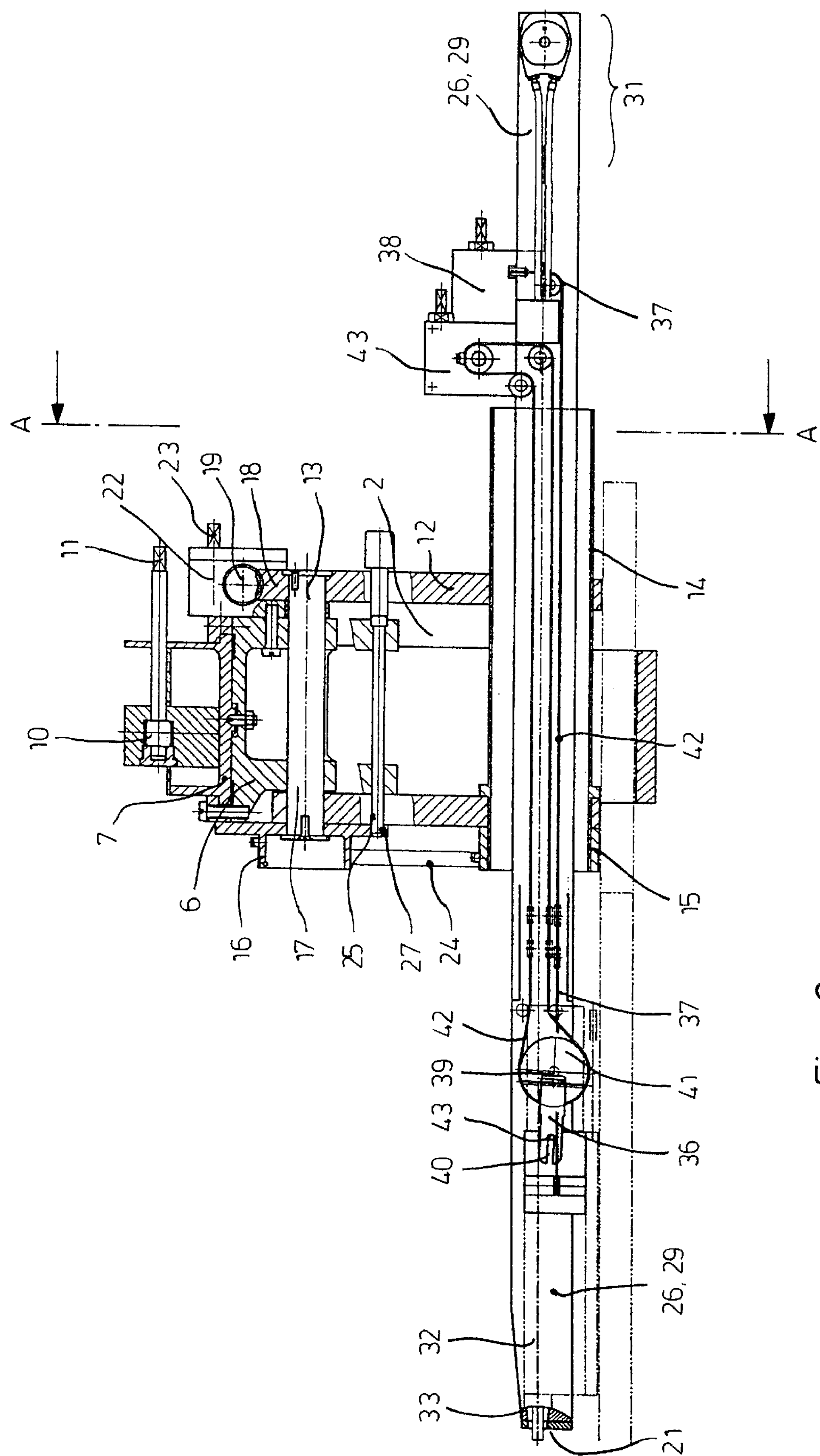
FIG. 2 is a top view of the manipulator.

Another important element of the manipulator is the housing 32, which is disposed in the inner space 28 so as to be pivotable horizontally and vertically about the spherical support calotte 33 and which exchangeably receives the instruments needed for treatment. In the particular use of the MRT for mammography, the instruments are a biopsy device with a trocar for taking a sample and an applicator of a laser apparatus for possible subsequent laser surgery. Adapters are provided for accommodating the respective devices and apparatus in the housing 32. The functions of the housing in cooperation with the instruments will be described in detail later on the basis of FIGS. 5 to 7. The housing 32 is so supported by the cable 33, that it pivots about a fixed point 35, which is outside the front end 21 of the manipulator. The point 35 is in the area where the tissue of the patient is penetrated so that the penetration point remains the same no matter in which way the angular position of the respective instrument is changed. Generally, an instrument is inserted through a trocar wherein then the trocar is subject to the movement constraints. The horizontal pivotability of the housing 32 is made possible by the arrow shape of the inner space 28 in which the housing 32 is disposed. Within the inner space 28, the housing 32 is pulled by elastic straps 34 toward the calotte 33, that is, its pivotal support area and is held in place by sidewardly pivotable support legs 36 which are rotatable about the axis 39. At a location remote from the pivotal support point of the housing 32, that is, as shown in FIG. 1 in the area between the point of engagement by the support legs 36 and the point of attachment of the elastic straps 34 cables 37 are attached to the housing 32, which cables extend, by way of several guide pulleys, to the pivot drive 38 at the proximal end 31 of the support tube 14 from where they can be operated to pivot the housing 32.

For a vertical pivot movement, pins 43 extending from the proximal end of the housing 32 slide in elongated slots 40 formed in the support legs 36. The legs are rotatably mounted on the inner side of the support arms 26 by pivot discs 41 so as to be pivotable about the axis 39 together with the pivot discs 41., Operating cables 42 extend from the pivot discs 41 to the drive 143 by way of several guide pulleys to provide for pivoting of the housing 32 in a vertical plane from the proximal end of the support tube 14 or the support arms 26 extending through the support tube 14. The pivotability of the housing 32 about the insertion point 35 permits a cross-section biopsy in any desired plane and also a subsequent laser therapy, depending on the instrument used.

As already mentioned, the housing 32 is an important element of the manipulator; it is the central unit from which the diagnostic-therapeutic procedures are functionally instigated. It is essential that the housing is supported by way of the spherical calotte 33 so that it pivots spatially about the fixed point 35. Within the housing 32, a drive carriage 48 is supported for linear movement in the z-direction that is in the longitudinal direction of the MRT channel 1. It serves for moving the instruments through the fixed point 35 into the tissue 51 to be treated. The axial movement of the drive carriage 48 can be controlled from the proximal end 31 of the arm 26 by elements, which are not shown in detail. At the distal end of the housing 32, a sterilization sleeve 49 is installed as a protective structure, which prevents contamination of the parts of the instrument entering the tissue 51.

Figure 5:
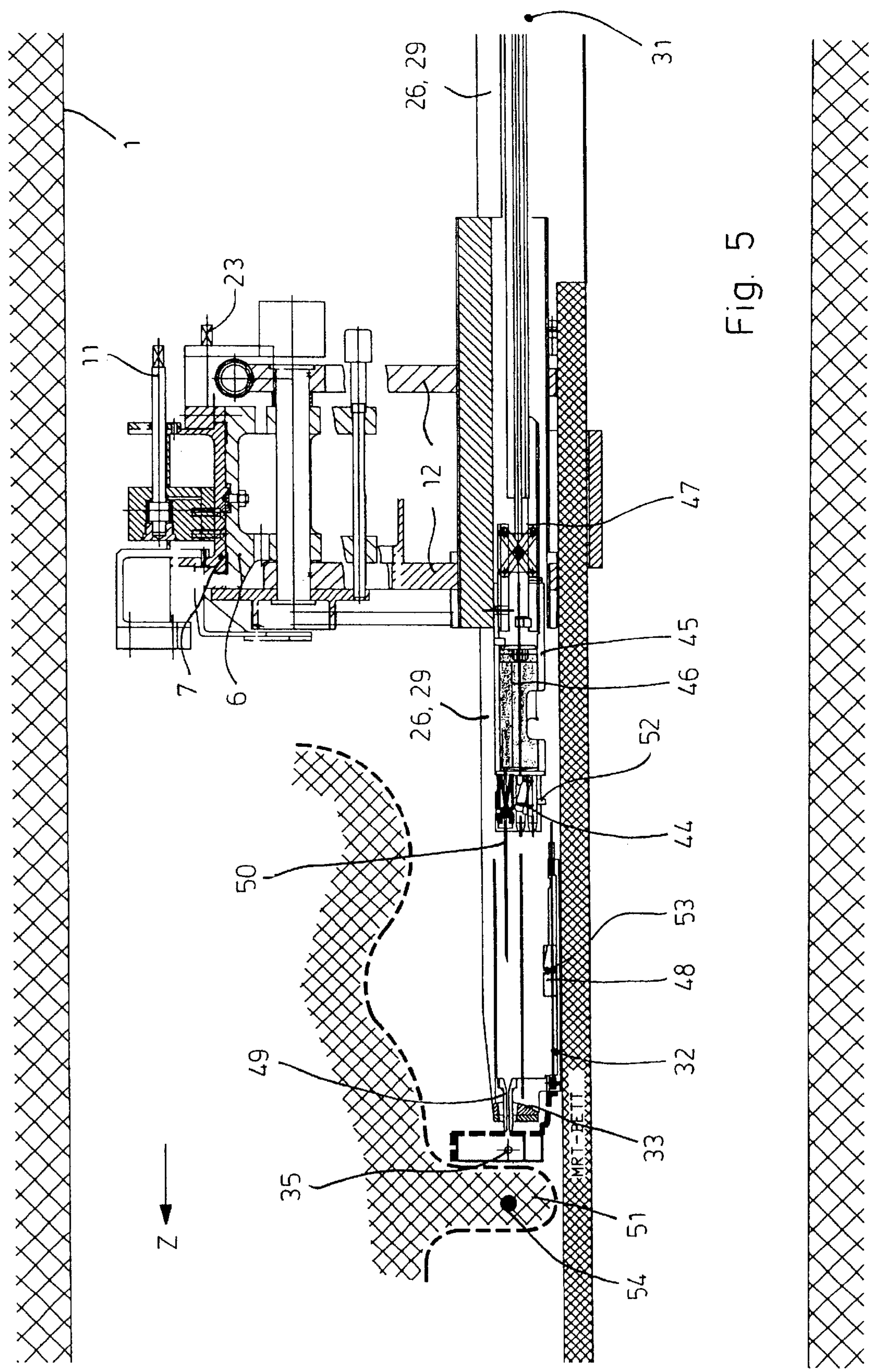
FIG. 5 shows the introduction motion of a diagnostic-therapeutic instrument into the MRT housing.
Figure 6:
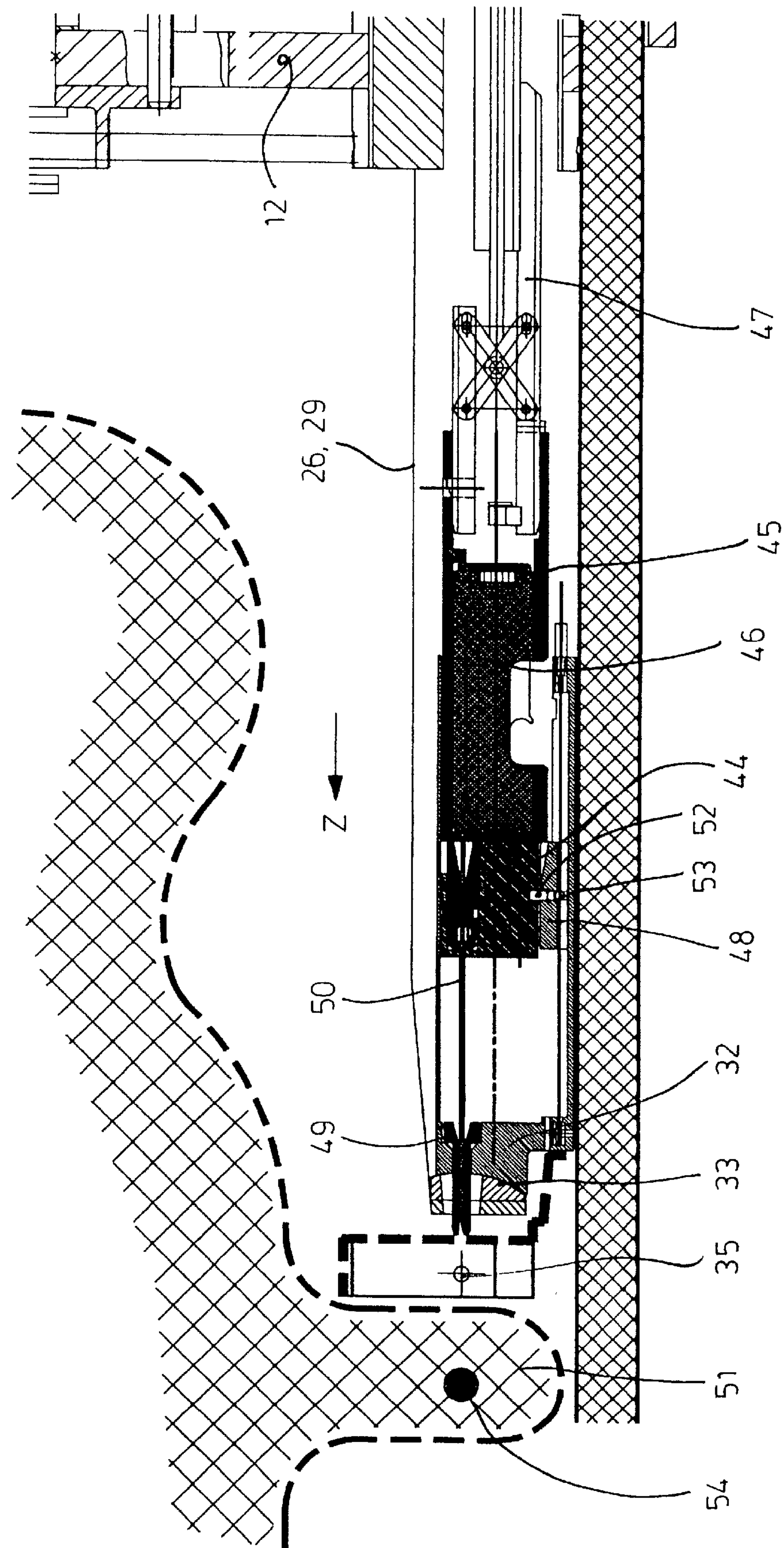
FIG. 6 shows the coupling procedure of a trocar receiver and of an instrument adapter to a drive within the housing.
Figure 7:
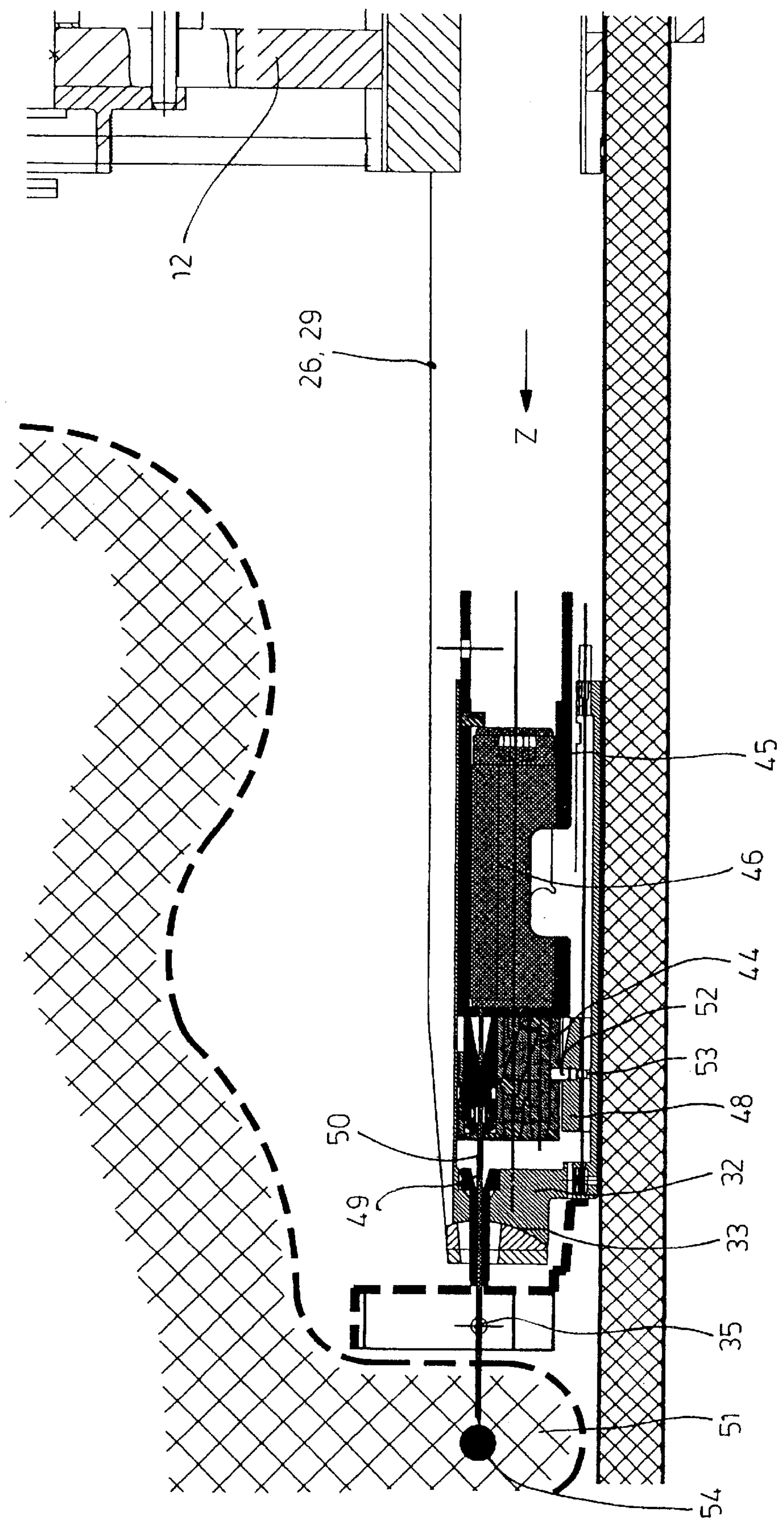
FIG. 7 shows the insertion of the diagnostic-therapeutic instrument into a fixed breast of a patient.

In the housing 32, there is disposed a movable trocar receiver 44 in whose upper part the trocar 50 is disposed in alignment with the sterilization sleeve 49. This trocar receiver 44 is supported so as to be slideable into the housing 32, where it can be coupled to the drive carriage 48. In FIG. 5, the trocar receiver 44 is shown before being inserted in, that is, it is shown removed from the housing 32. In FIGS. 6 and 7, the trocar receiver is shown in different positions in the housing 32. At the proximal end of the trocar receiver 44, a hollow instrument adapter 45 is disposed between the support arms 26, which instrument adapter receives a respective instrument 46 as needed for a particular procedure. When coupled to the drive carriage 48, the trocar receiver 44 forms the connecting element between the drive carriage 48 and the instrument adapter 45 which, as a result, is also movable in the housing 32 by the carriage 48 from the proximal end 31. By the coupling of the three components drive carriage 48, instrument adapter 45 and trocar 50, the instruments 46 in the instrument adapter 45 can be moved in the z-direction. The trocar 50 acts as a guide canal and forms a shield for the protection of the healthy tissue from contamination by potential cancer cells during a change of the instruments.

As already mentioned, the instrument adapter 45 serves for the adaptation and the handling of different instruments. At its end adjacent the trocar receiver 44, it includes a coupling mechanism which permits its coupling to, or uncoupling from, the trocar receiver 44 and which therefore allows a change of instruments while the trocar 50 remains in place. The instruments 46 comprise various diagnostic and therapeutic instruments, for example, a biopsy apparatus as a diagnostic instrument and an adapted laser head as a therapeutic instrument. At the proximal end of the instrument adapter 45, there is provided a handling device 47, which is also movable between the support arms 26 in the z-direction and by which the instruments can be moved into, and out of, the housing 32.

Operation of the manipulator in connection with a MR apparatus.

Mammography is performed as follows:

The breast of a patient who rests in the channel 1 on her stomach is positioned in the isocenter of the MRT in the area of the windows 20. The manipulator is introduced into the channel 1 toward the patient such that its front end 21 is disposed adjacent the isocenter. It is fixed in place by the clamping device 4. The planigraphs are taken in the conventional manner. The target coordinates of any possible cancer location found are recorded. If a biopsy is to be performed to examine a possible cancer formation, the drive shafts 11, 23 and the drives 38 and 43 are connected to a drive unit (not shown) which is controlled by a control unit on the basis of the target coordinates. The target coordinates are converted to manipulator coordinates corresponding to the windows 20 and the manipulator position is adjusted corresponding to the coordinates in the x/y plane by movement of the carriage 6 and rotation about the axis 13. The positioning in the z-axis, that is in depth, is performed by a predetermined insertion depth movement of the trocar out of the housing 32. Then the biopsy apparatus is placed at the proximal end 31 between the side members 29 of the support arm 26 and is moved with the handling device 47 shown in FIGS. 5 to 7 into the housing 32. After taking the biopsy, the biopsy apparatus is again retracted. For possible further treatment, the biopsy apparatus is then replaced by a laser applicator. The laser applicator is inserted into the housing 32 in the same manner as the biopsy apparatus while the housing 32 remains positioned in accordance with the target coordinates. In this fixed position, laser energy is then applied depending on the size of a tumor detected.

Operation of some of the elements within and at the housing 32:

First, the sterilization sleeve 49 is inserted into the housing 32 with a grasping device, which is not shown. Then the trocar 50 is inserted into the trocar receiver 44 and an instrument is positioned in the instrument adapter 45, while the manipulator is outside the MRT channel 1. The trocar receiver 44 and the instrument adapter are then coupled and moved into guides between the side members 29 of the manipulator at the proximal end 31 thereof. Subsequently, the handling device 47 is moved into the open end of the instrument adapter 45 and is locked therein. In the next step, the components connected to the handling device 47 are advanced into the housing 32. During the last part of this advancement, the trocar receiver 44 moves over the drive carriage 48. In a predetermined position, the trocar receiver 44 and the drive carriage 48 are locked together. The locking is achieved by the engagement of a locking member 52, which is provided on the trocar receiver 44 and which extends into a recess 53 in the drive carriage 48. After this step, the handling device 47 is unlocked from the instrument adapter 45 and is pulled out of the manipulator at the end 31 thereof. The manipulator can now move toward the x/y location of the area 54 to be treated in the manner described earlier. When that location is reached the instrument 46 is inserted into the tissue 51 by advancement of the drive carriage 48.

Any change of instruments 46 occurs while the trocar 50 remains in place. For such an instrument exchange the instrument adapter 45 is uncoupled from the trocar receiver 44 and retracted by a certain distance. This is done by way of a cable, preferably a Bowden wire, from without the MRT. Now the instrument adapter 45 can be pulled out of the manipulator by the handling device 47 and can then be reinserted after installation of another instrument. At the end of the treatment, the instrument adapter 45 is not uncoupled from the trocar receiver 44, but rather the lock between the trocar receiver 44 and the drive carriage 48 is released. With the retraction of the handling device 47, all the components initially installed in the manipulator are then removed together.

What is claimed is:

1. A magnetic resonance tomograph (MRT) with a continuous channel for the insertion from one end thereof of a stretcher adapted to support a female patient laying on her stomach for the performance of a MR mammography, comprising: a manipulator for introducing into said channel from the opposite end thereof in a direction parallel to the longitudinal axis of said channel, instruments for providing an image-supported diagnosis and for a therapeutic treatment of a breast of said patient, said manipulator being position-adjustable with respect to said breast in all three spatial directions about a point on the surface of said breast for proper angular positioning of the instruments, and including a support arm having a distal end with a housing for receiving different instruments, which can be exchangeably inserted from the other (proximal) end of said support arm for use in connection with different treatment steps, said manipulator comprising a bow-like frame with support skids disposed on opposite sides for supporting said frame on, and sliding it into, said channel on support rails with which said frame is lockable when properly positioned in said channel, said frame having an upper portion in the form of a horizontal bridge, a support carriage supported from said bridge so as to be movable along said bridge in the x-direction, operating means for moving said carriage along said bridge, pivot arms pivotally supported at one end on said support carriage and supporting at their other end said support arm within said housing, drive means for pivoting said pivot arms about a pivot axis whereby its other end with said housing including the instruments is movable in the y-direction in a plane extending transverse to the channel axis for properly positioning said housing with said instruments relative to said breast, said housing including a drive carriage operable from the proximate end of said manipulator for advancing said instruments from, or retracting then into, said housing, and a handling device for inserting said instruments into and removing them from, said housing and for moving said housing into a position for proper operation of said instruments.

2. The manipulator according to claim 1, wherein said housing is pivotally supported so as to pivot operated by cables, about a fixed point disposed outside the housing in front of the distal front end of the manipulator and at the surface of the breast to be examined.

3. The manipulator according to claim 2, wherein said support arm mounted to the other end of said pivot arms has a distal end which forms the front end of said manipulator and defines rearwardly a conically widening space receiving said housing and accommodating any pivot movement thereof about said fixed point.

4. The manipulator according to claim 1, wherein said housing forms a movable trocar receiver having an upper part in which a trocar is disposed, said trocar receiver including coupling means for connection with said drive carriage so as to be movable by said drive carriage.

5. The manipulator according to claim 4, wherein, adjacent said trocar receiver, an instrument adapter is disposed into which a particular instrument needed can be placed, said trocar receiver, when coupled to said drive carriage, forming a connecting element between the drive carriage and the instrument adapter which thereby is movable in unison with the drive carriage in the housing, and said handling device being disposed in the manipulator adjacent the instrument adapter and being movable from the proximal end together with the components connected to the instrument adapter, the handling device being lockable to the instrument adapter.

* * * * *